(12) United States Patent
Norenberg

(10) Patent No.: US 7,685,865 B2
(45) Date of Patent: Mar. 30, 2010

(54) METHOD AND APPARATUS FOR MEASURING THE RATE OF PERMEATION

(75) Inventor: Holger Norenberg, Oxford (GB)

(73) Assignee: Technolox Ltd., Oxford (GB)

( * ) Notice: Subject to any disclaimer, the term of this patent is extended or adjusted under 35 U.S.C. 154(b) by 234 days.

(21) Appl. No.: 11/687,208

(22) Filed: Mar. 16, 2007

(65) Prior Publication Data

US 2007/0227233 A1    Oct. 4, 2007

(30) Foreign Application Priority Data

Mar. 30, 2006    (GB)    ................................ 0606327.5

(51) Int. Cl.
*G01N 15/08* (2006.01)
(52) U.S. Cl. ........................................................ 73/38
(58) Field of Classification Search ...................... 73/38
See application file for complete search history.

(56) References Cited

U.S. PATENT DOCUMENTS 6,766,682 B2 *    7/2004    Engle et al. .................... 73/38

2006/0005608 A1 *    1/2006    Kitzhoffer et al. ............. 73/38

OTHER PUBLICATIONS

Norenberg, H. et al. "Mass spectrometric estimation of gas permeation coefficients for thin polymer membranes." Review of Scientific Instruments. vol. 70, No. 5 (May 1999), pp. 2414-2420.*

* cited by examiner

*Primary Examiner*—Hezron Williams
*Assistant Examiner*—Nathaniel Kolb

(57) ABSTRACT

A method and an apparatus are provided for measuring the rate of permeation of a gas or vapour through a test sample with the gas container detachable from the sensor. The gas container consists of an upstream and a downstream chamber in communication with a test sample. The upstream chamber of the gas container containing the test sample is filled with a gas or vapour. The pressure increase in the downstream chamber is monitored and recorded at successive increments of time. To estimate the rate of permeation one or more experimental pressure values can be used as input for a mathematical approximation procedure. Using the starting pressure and one or more pressure values taken at different times allows the gas container with the test sample to be detached from the sensor and hence an increased sample throughput is realised.

5 Claims, 9 Drawing Sheets

METHOD AND APPARATUS FOR MEASURING THE RATE OF PERMEATION

CROSS-REFERENCE TO RELATED APPLICATIONS

This application is based upon and claims the benefits of priority from the prior UK patent application entitled: "Method and device for measuring the rate of permeation" no. 0606327.5 filed 30 Mar. 2006. The content of this application is incorporated by reference.

BACKGROUND OF THE INVENTION

1. Field of the Invention

This invention relates to the measurement of the rate of permeation of a gas or vapour through a sample of a material.

2. Description of the Related Art

Permeation describes the process of species entering, moving through and leaving a test sample. Measuring the rate of permeation (or strictly speaking the rate of transmission) of vapours and gases through materials, in particular barrier materials, is important in various fields. Examples are packaging of food, of medical supplies, of electronic components and as membranes in fuel cells. Barrier layers serve the purpose of preventing or restricting the passing of a gas or a vapour.

A number of methods are known to measure the rate of permeation.

U.S. Pat. No. 2,755,660, JP 63132137A and ASTM standard D1434-82(2003) describe a method where one side of the test sample is kept at a constant pressure and the pressure increase on the other side of the sample is measured.

U.S. Pat. No. 5,390,539 and ASTM standard F1249-05 describe the use of electrochemical and infrared sensors for the detection of oxygen and water vapour.

US2002/0173922A1 describes a sophisticated method combining an acoustic wave and optical detection method where the barrier layer for permeation measurements needs to be deposited onto a transducer, followed by an elaborate measuring procedure consisting of many steps.

EP 1373861A2 describes the "Calcium test" where the progress of corrosion of a thin layer of calcium deposited on the test sample is taken as measure for the amount of water or oxygen that has passed through the test sample.

U.S. Pat. No. 6,909,088 describes a mass-spectrometric method for measuring the rate of permeation.

U.S. Pat. No. 6,804,989 describes a very sensitive method to detect water vapour permeation by using radioactive water.

U.S. Pat. Nos. 4,858,461 and 5,081,863 describe a multi-chamber setup, which requires continuous gas flow; stack arrangements have been suggested too (U.S. Pat. No. 4,468,951).

U.S. Pat. No. 5,591,898 describes a method using a carrier gas to calculate the permeability P as product of the measured coefficient of diffusion D and the solubility S.

All methods described in the art have the detecting means attached to the assembly with the test sample. Despite all the effort that has gone in the invention of these methods and apparatuses they suffer from serious drawbacks. The proximity between test sample and sensor limits the parameter range of testing, because the sensors are usually not rated to high temperatures. Another disadvantage is the limited sample throughput as continuous measurement even in an arrangement with multiple cells requires the detector in attendance of the test sample over substantial periods of time. Using a carrier gas makes the experimental set-up more cumbersome and costly.

BRIEF SUMMARY OF THE INVENTION

To alleviate these problems, the present invention describes a method with an algorithm for data evaluation and an apparatus for measurement of the rate of permeation of gases and vapours through a test sample made of a material. "Gas container" describes a vessel that can contain a gas or a vapour or a mixture thereof and the test sample. "Permeation" describes the transmission of gases or vapours through a test sample. The test sample can be made of a polymer, a metal, a ceramic material, a composite, a semiconductor, a biological material or a combination thereof). "Outgassing" describes the flow of gas or vapour from inside the test sample to the outside.

A method with an algorithm for data evaluation and an apparatus are provided to measure the rate of permeation of gases or vapours through a test sample made of a material comprising:

Providing a test sample between an upstream chamber and a downstream chamber in a gas container filling the upstream chamber of the gas container with an amount of gas or vapour creating a pressure difference between the upstream chamber and the downstream chamber arranging the gas container with the test sample to communicate with a pressure sensor providing a means of detaching the upstream and downstream chambers with the test sample from the pressure sensor measuring the pressure in the downstream chamber of the gas container concluding the rate of permeation The invention has the main advantage of an increased sample throughput and a wider parameter range of measurement, in particular a much increased temperature range. The advantage of this method is its simplicity.

Another advantage is that a variety of gas containers can be used and that each gas container may be adapted to specific requirements, for instance, to accommodate samples of a different size.

Another advantage is that the method can be used to measure the rate of permeation of gases and vapours.

Yet another advantage is that the method can be run in conventional mode, for example the manometric method according to ASTM D 1434-82(2003).

The lack of a carrier gas simplifies the experimental set-up and gives a cost advantage.

BRIEF DESCRIPTION OF THE SEVERAL VIEWS OF DRAWINGS

A method as specific embodiment of the invention will now be described by way of non-limiting example with reference to the accompanying drawings in which.

Figure 6:
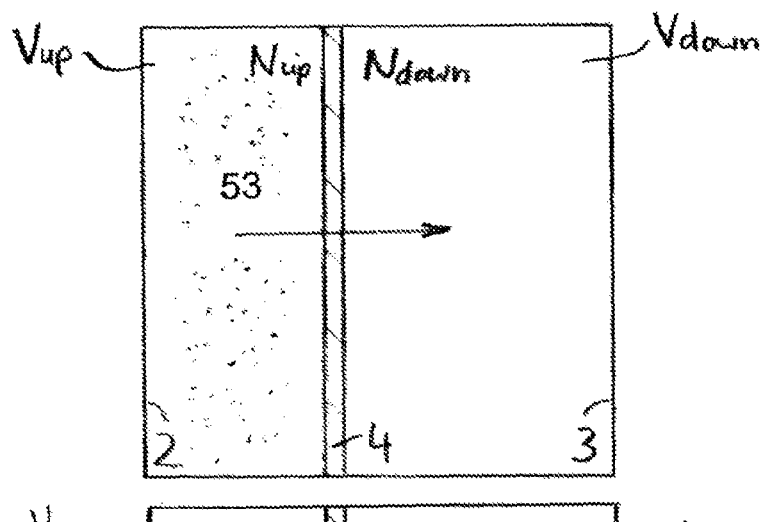
Figure 7:
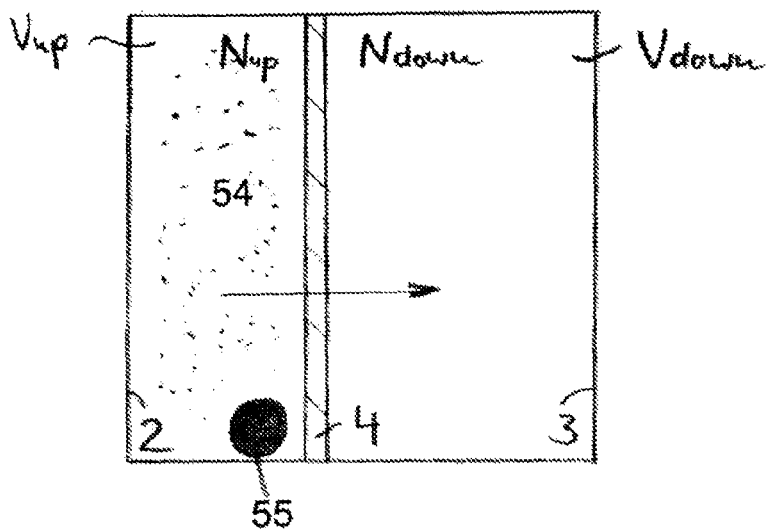
Figure 8:
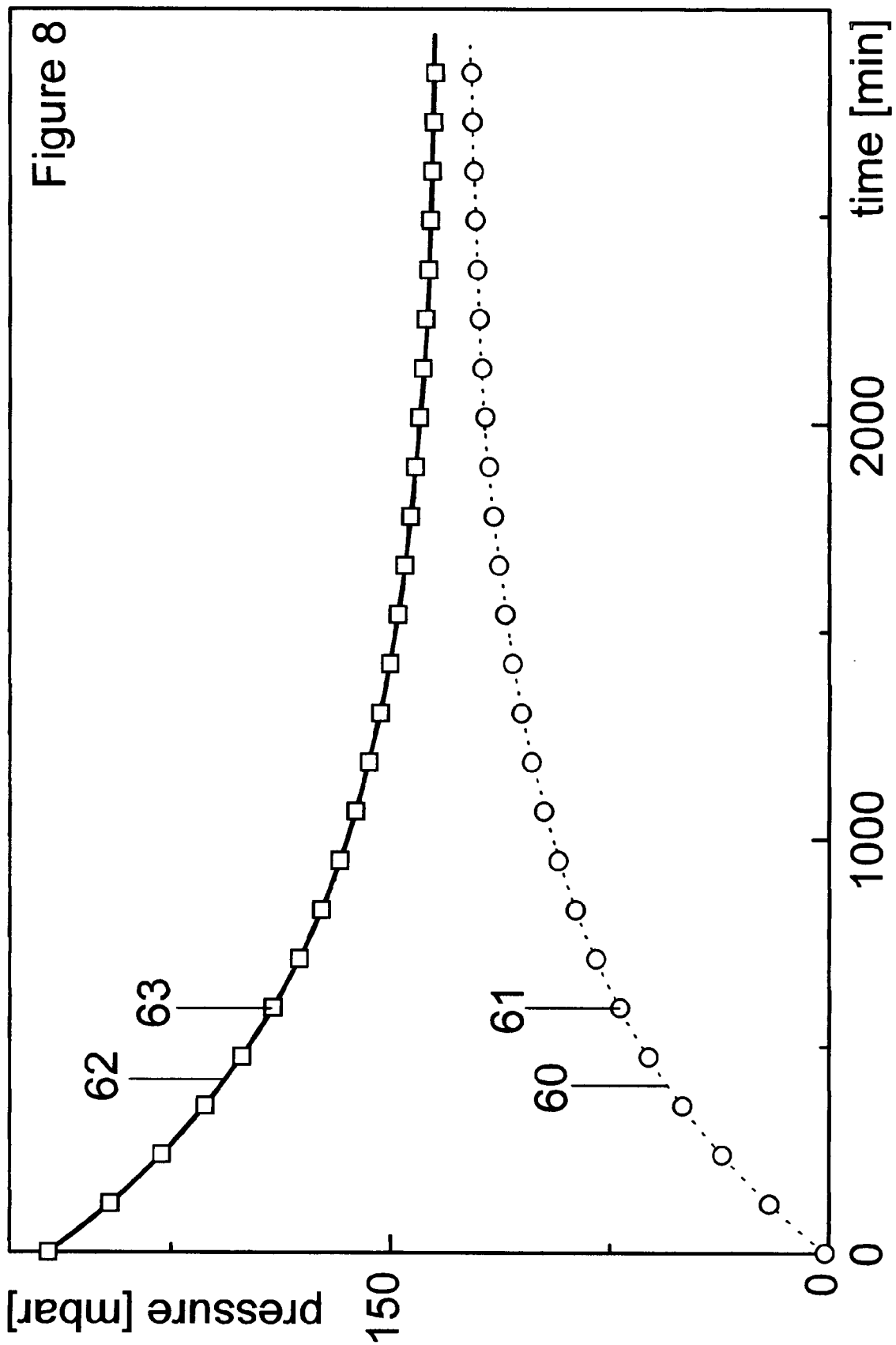
Figure 9:
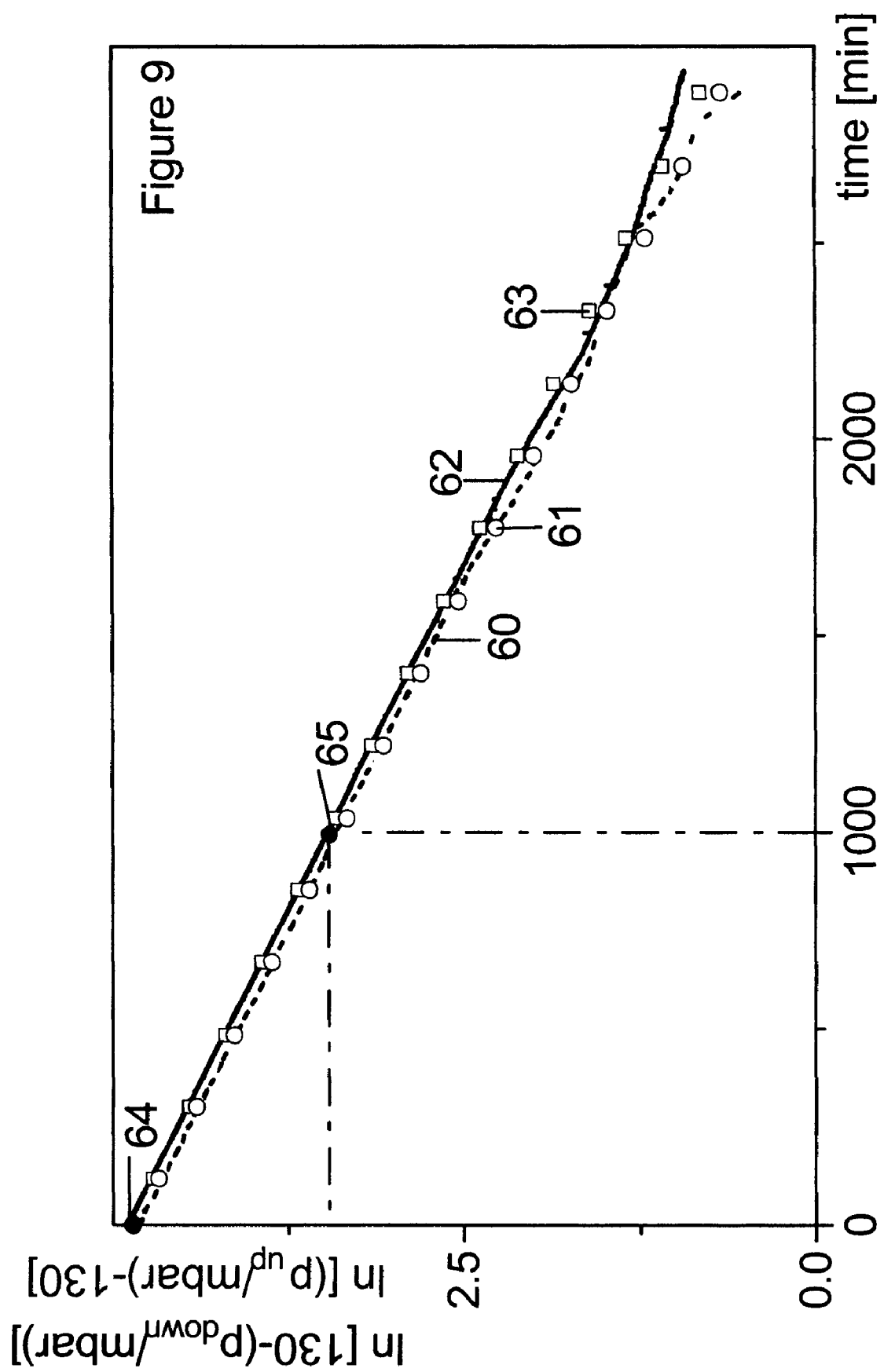
Figure 10:
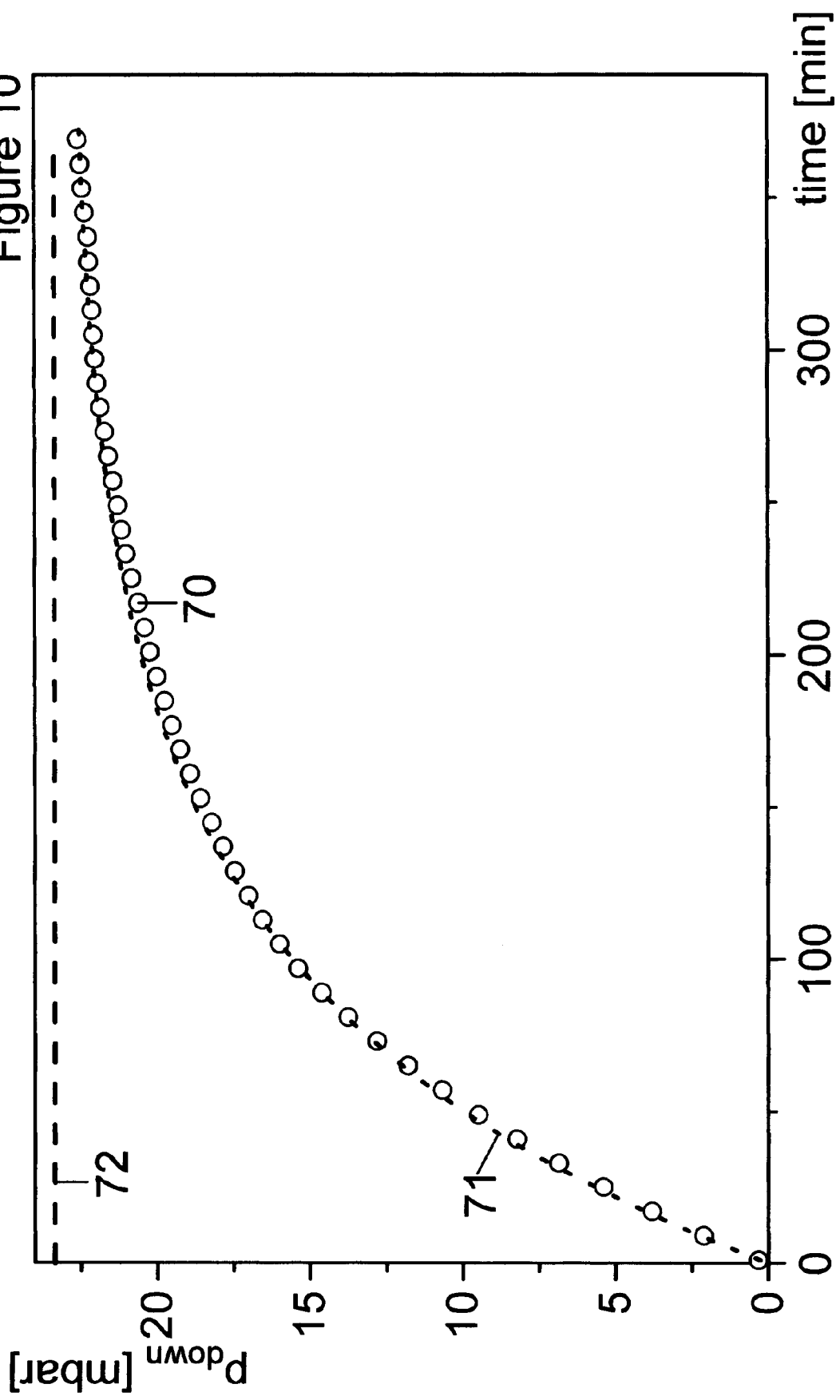
Figure 11:
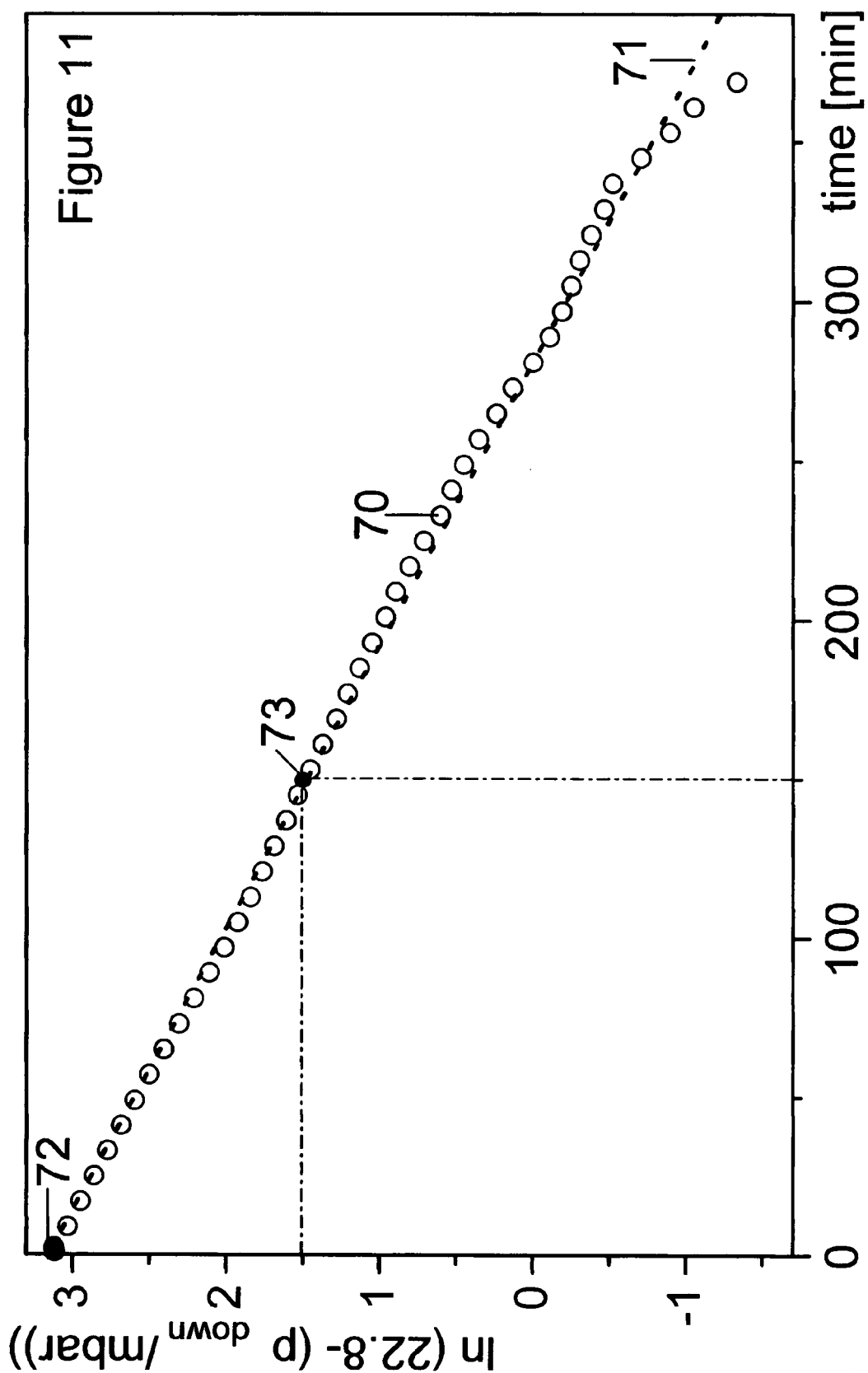
Figure 12:
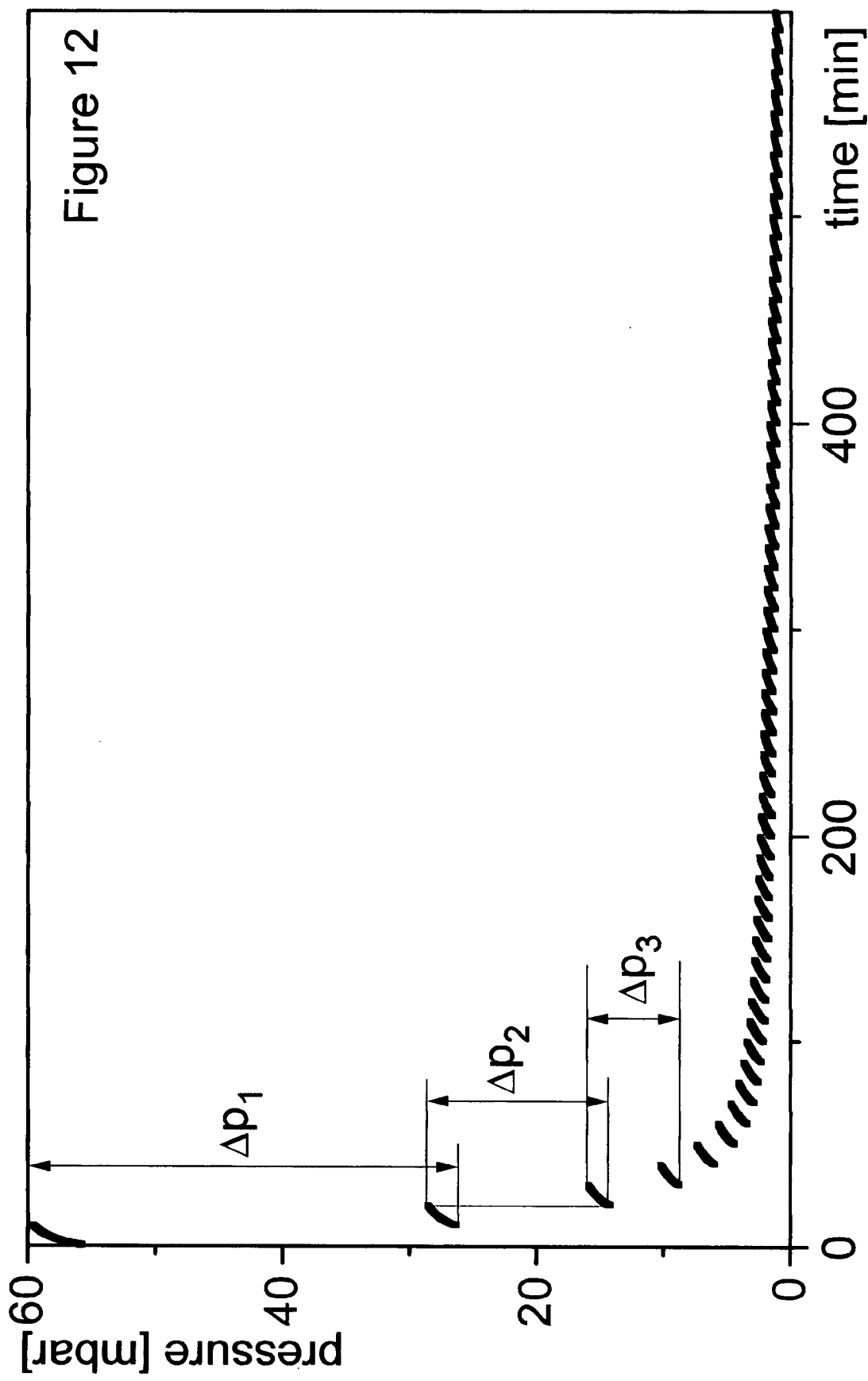

FIG. 6 shows a diagrammatic view of the principle of permeation of a gas through a test sample FIG. 7 shows a diagrammatic view of the principle of permeation of a vapour created over a liquid through a test sample FIG. 8 shows the downstream and upstream pressure recorded during a measurement of oxygen permeation through a film of oriented polypropylene, 60 µm thick and values derived from a fit with an exponential function FIG. 9 shows the downstream pressure as described for FIG. 8 in a logarithmic representation FIG. 10 shows the downstream pressure recorded during a measurement of water vapour permeation through a film of polyethylene terephthalate (PET) 38 µm thick and values derived from a fit of the experimental data with an exponential function FIG. 11 shows the pressure in the downstream chamber as described for FIG. 10 in a logarithmic representation FIG. 12 shows the pressure in the downstream chamber as function of time for an outgassing experiment on polyethylene naphthalate (PEN)

Figure 13:
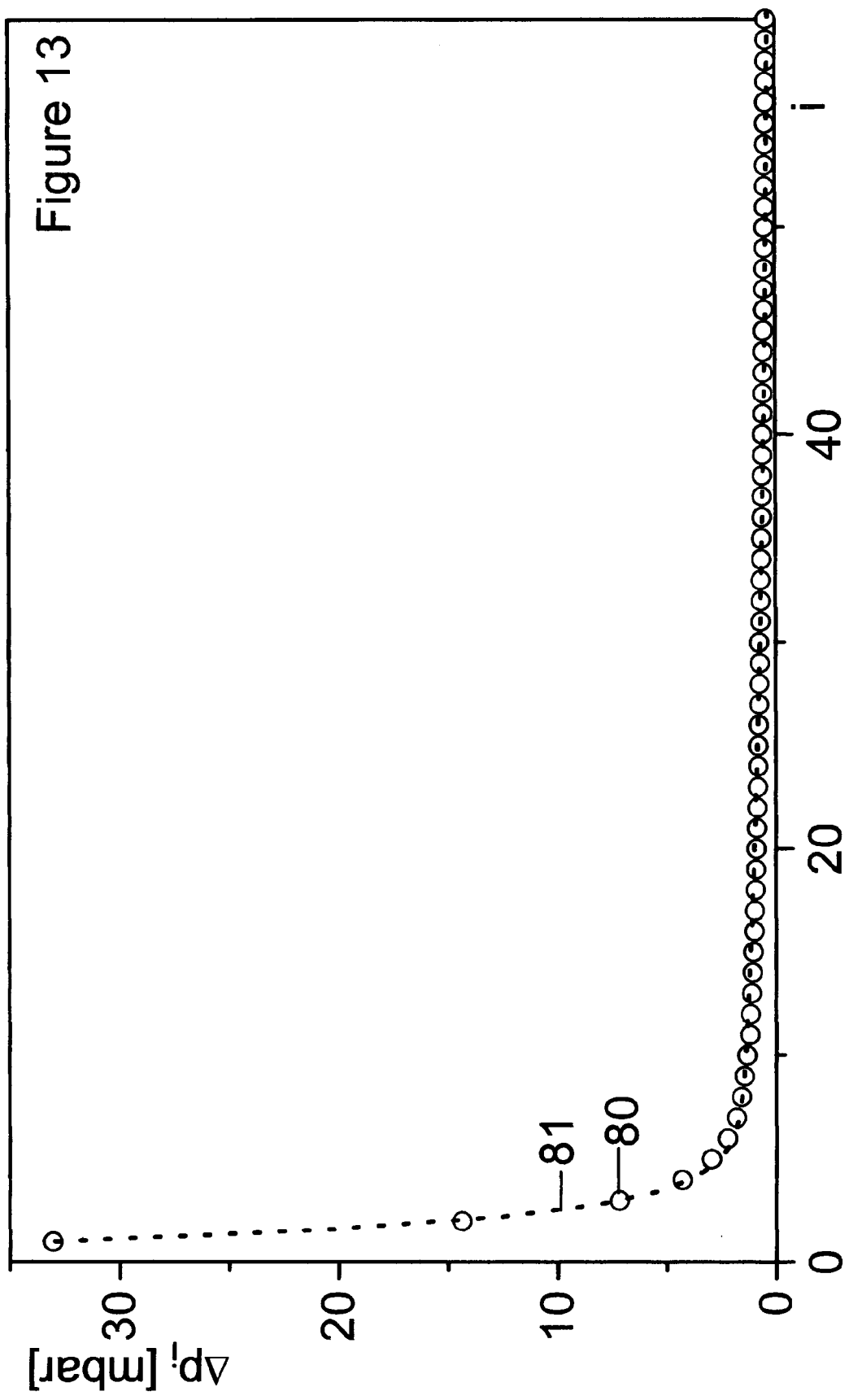

FIG. 13 shows the pressure decrease in the downstream chamber after subsequent cycles of pumping, data obtained from FIG. 12

DETAILED DESCRIPTION OF THE INVENTION

The current invention describes a method to measure the rate of permeation for gases and vapours under variable pressure conditions. This allows detaching the test sample from gas or vapour sources during the permeation measurement because filling with gas or vapour is required only at the beginning. A mathematical algorithm is provided, which allows the determination of the rate of permeation either from data taken continuously during the experiment or from one or more data taken at suitable times during the experiment. Taking pressure readings not continuously allows detaching the test sample from the pressure sensor. This way, several test samples can be exposed to permeant gases or vapours simultaneously. At suitable times they can be connected to the sensor in turn to take a reading.

In the "Experiments" chapter the method and an apparatus are described. The "Calculation" chapter explains the algorithm of evaluating the measured data and the "Examples" section further illustrates the method with experimental data.

1. Experiments

The purpose of the experiment is the measurement of the rate of permeation of a gas or a vapour through a test sample. The measured quantity is a pressure change caused by permeation. This pressure change and known parameters of the experiment are used to obtain the rate of permeation.

Figure 1:
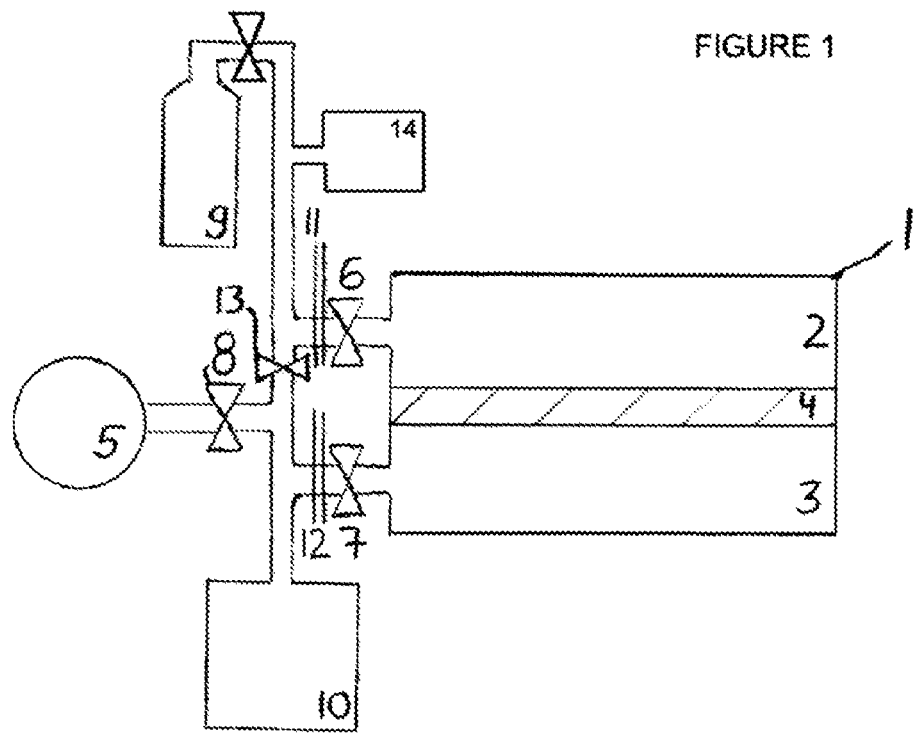
FIG. 1 shows a diagrammatic view of an apparatus

FIG. 1 shows a diagrammatic view of the device with the gas container 1 consisting of an upstream chamber 2 and a downstream chamber 3. The gas container in this and the alternative implementations should be made of an impermeable material. The test sample 4 is positioned between the two chambers 2 and 3 separating them. Gas or vapour going from one chamber to the other permeates through the test sample 4. Initially, both chambers 2 and 3 are under vacuum. To lower the pressure to a sufficiently low vacuum level in either or both chambers 2 and 3, a vacuum pump 5 and valves 6, 7 and 8 are provided.

With valve 6 open and valve 13 closed the upstream chamber 2 is then filled with the gas or vapour to be studied by means of a filling facility 9, which can be a conventional gas cylinder with a valve or a liquid reservoir in the case of vapours. The gas filling facility 9 may have a conventional sensor to show the pressure in the upstream chamber 2 or a separate sensor 14 may be provided to monitor the pressure in the upstream chamber 2. After the filling of the upstream chamber 2 at the desired pressure is complete, valve 6 is closed. The gas or vapour permeates from the upstream chamber 2 through the test sample 4 into the downstream chamber 3 where it causes a pressure increase, which can be monitored by a sensor 10 (valve 7 open, valves 8 and 13 closed).

Two fittings 11 and 12 are provided to detach the gas container 1 from the rest of the assembly with sensor 10 and vacuum pump 5 (valves 6 and 7 closed). The detached gas container 1 can then be transferred to undergo treatment such as exposure to elevated temperatures. The advantage is an increased sample throughput as more than one gas container can be used with the same pressure sensor and vacuum pump.

Another advantage of the method is that by keeping the sensor 10 in continuous communication with the downstream chamber 3 (valves 8, 13 closed, valve 7 open) and keeping a constant gas pressure in the upstream chamber 2, it can be run in conventional time-lag mode permitting comparison to earlier measurements or other permeation testing apparatuses.

Figure 2:
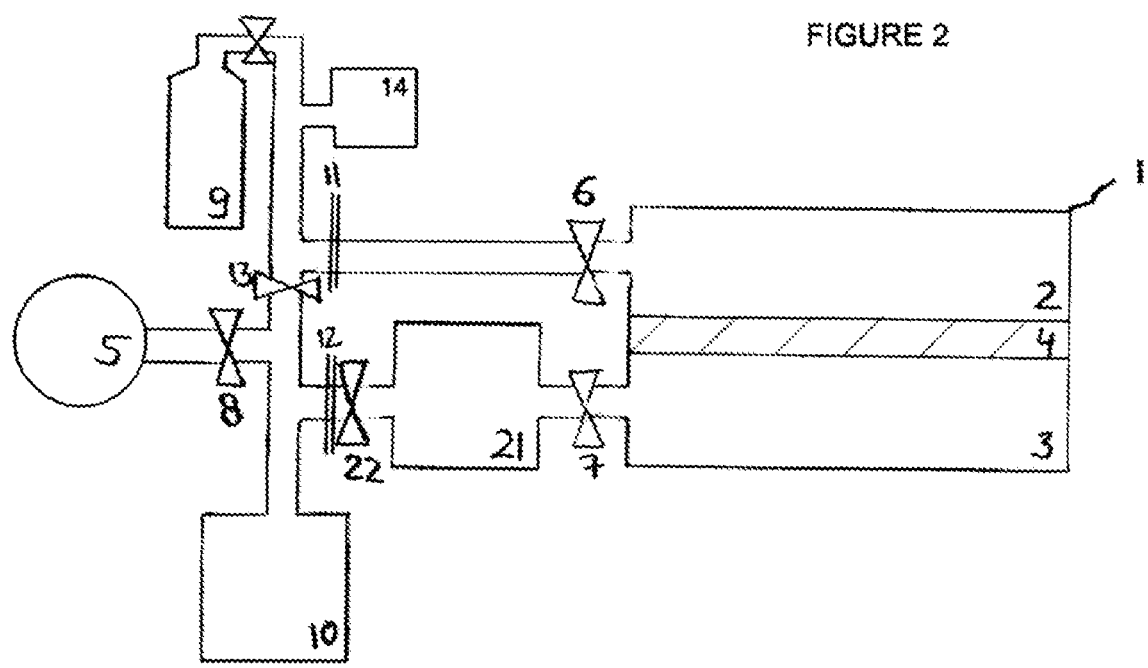
FIG. 2 shows a diagrammatic view of the first alternative of an apparatus

FIG. 2 shows a first alternative of the apparatus. The advantage of this device is its increased accuracy. The increased accuracy is achieved by adding a collection chamber 21 and a valve 22. A collection chamber 21 is desirable for permeation measurements at high temperatures, where the gas container 1 has to cool down before handling is possible. Because of the changing temperature during this stage the rate of permeation is not constant and hence difficult to estimate. The collection chamber 21 collects gas or vapour that has permeated through the test sample 4 at constant temperature (valve 7 open) but keeps out gas or vapour that has permeated at a changing temperature (valve 7 closed).

Figure 3:
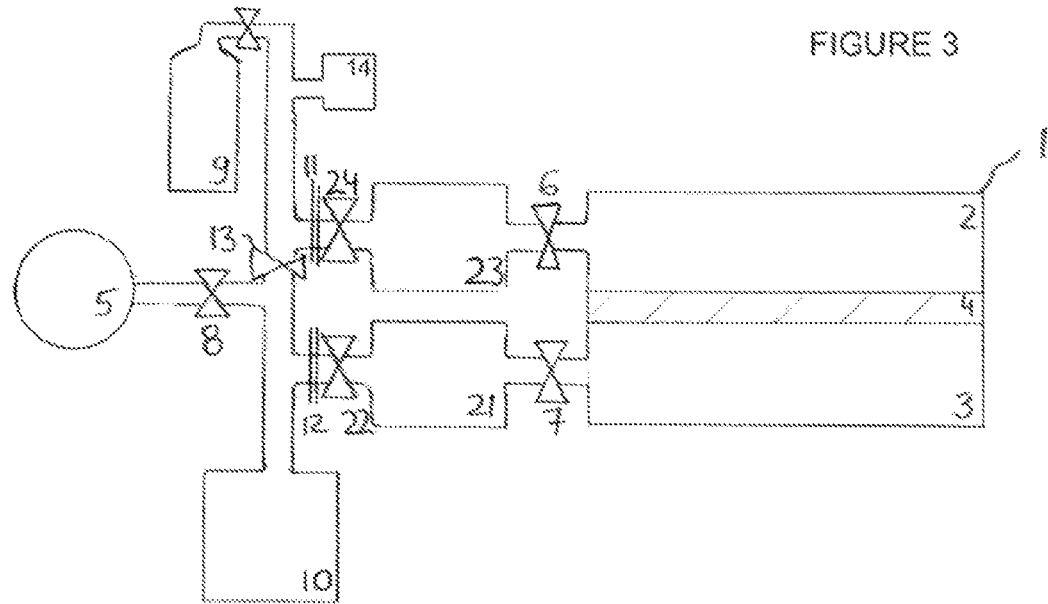
FIG. 3 shows a diagrammatic view of the second alternative of an apparatus

FIG. 3 shows a second alternative of the device. The advantage of this device is its further increased accuracy. The increased accuracy is achieved by adding a reservoir chamber 23 filled with a well defined amount of gas or vapour, and a valve 24. A reservoir chamber 23 is desirable for permeation measurement at high temperatures, where it takes time for the gas container 1 with the test sample 4 to reach a preset temperature. Because of the changing temperature during this stage the rate of permeation is not constant. The upstream chamber 2 is kept at a sufficiently low vacuum level while the temperature of the test sample 4 is changing prior to exposure to gas or vacuum. After reaching a sufficiently constant temperature gas or vapour from the reservoir chamber 23 is released into the upstream chamber 2 by opening the hitherto closed valve 24.

Figure 4:
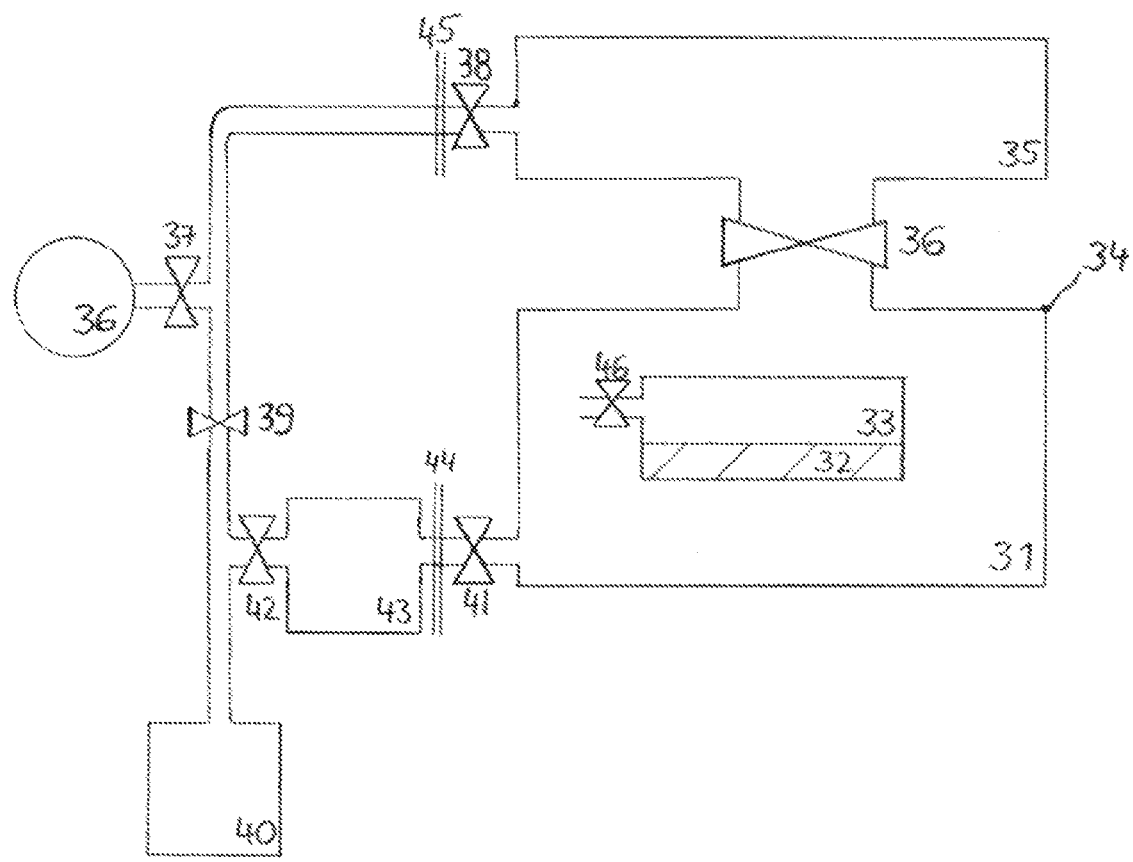
FIG. 4 shows a diagrammatic view of the third alternative of an apparatus

FIG. 4 shows a third alternative of the device. The advantage is the further increased accuracy by reducing the level of background pressure in the downstream chamber 31 by constantly keeping it at a sufficiently low vacuum level. The test sample 32 is attached to the upstream chamber 33 and permeation takes place from the upstream chamber 33 through the test sample 32 to the downstream chamber 31. The upstream chamber 33 is filled by conventional means with gas or vapour outside the gas container 34, for instance through a valve 46. The gas container 34 comprises the downstream chamber 31 and a load-lock chamber 35. The downstream chamber 31 and the load-lock chamber are separated by a valve 36. After filling the upstream chamber is introduced into the load-lock chamber 35, which is then evacuated by a vacuum pump 36 through the then open valves valve 37 and 38 with valve 39 closed. After reaching a sufficiently low vacuum level in the load-lock chamber 35, valve 36 is opened and the upstream chamber 33 is transferred into the downstream chamber 31. Permeation of gas or vapour from the upstream chamber 33 through the test sample 32 causes a pressure increase in the downstream chamber 31, which can be monitored continuously by a pressure sensor 40 with valves 41, 42 open and 39 closed. Similar to the arrangement shown in FIG. 3 a collection chamber 43 with valve 42 can be used to increase the accuracy of the measurement. Fittings 44 and 45 are provided to detach the gas container 34 from the pressure sensor 40 and the vacuum pump 36.

Figure 5:
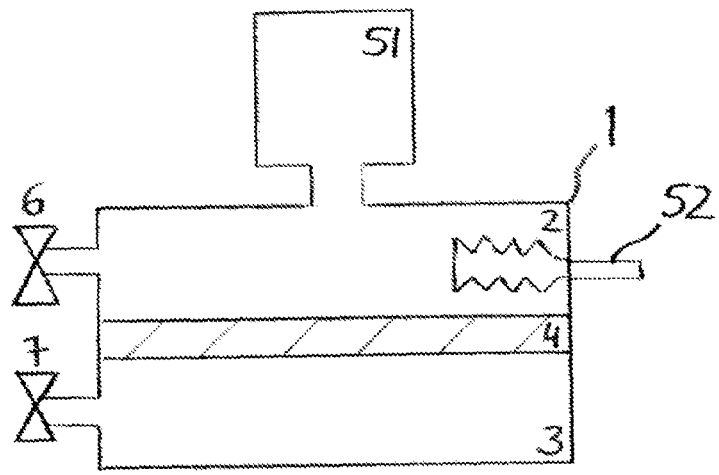
FIG. 5 shows a diagrammatic view of the fourth alternative of an apparatus

FIG. 5 shows a fourth alternative of the device. The advantage is that the pressure in the upstream chamber can be varied and measurements at different upstream pressures can be carried out without interfering with the test sample. A pressure sensor 51 and a volume changing device 52 are provided. The pressure changing device 52 could be a bellow, which extends into the upstream chamber 2. By moving the volume changing device 52 the pressure in the upstream chamber 2 can be changed. A pressure sensor 51 is provided to monitor the pressure in the upstream chamber 2. Instead of the pressure sensor 51 an arrangement similar to FIG. 1 with pressure sensor 14 can be used. If the volume changing device 52 is calibrated, for instance by relating its travel distance to the change of the pressure in the upstream chamber 2, no pressure sensor may be required.

The sensor to measure the pressure can be any pressure sensor. In a preferred embodiment a capacitance diaphragm sensor has been found to give good results. If a mix of permeated species is to be detected or if the sample is expected to show a strong outgassing, a sensor like a mass spectrometer, which is able to distinguish between different species, may be of advantage. Other sensors for example infrared sensors may be used instead of pressure sensors.

If the initial amount of gas or vapour in the upstream chamber 2 and downstream chamber 3 is negligible compared to the amount of gas or vapour contained in the test sample 4, the pressure increase detected by the sensors 10 and 14 is caused by gas or vapour originating in the test sample 4. Repeated evacuation of the chambers 2 and 3 after some time of outgassing and adding up the measured pressure increases will improve the accuracy of the measurement. As known from the prior art the permeability P can be expressed as the product of the constant of diffusion D and the solubility S: $P=D \cdot S$. This relationship can be used to calculate the permeability if D is known. Alternatively, if P and S are known from experiments described in this invention, the constant of diffusion D can be calculated.

The present invention is particularly suitable for test samples consisting of films which are sufficiently thin so that permeation through the edges is negligible compared to permeation across the major faces of the test sample 4.

2. Calculations

The requirement of detaching the gas container 1 with the test sample 4 from other components of the assembly such as sensors 10 and 14, gas filling facility 9 and pumps 5 requires a data evaluation algorithm, which takes a variable pressure in the upstream chamber 2 into account.

FIG. 6 illustrates the permeation process for gases. The upstream chamber 2 is initially filled with gas 53 at the desired pressure. The gas permeates through the test sample 4 into the downstream chamber 3. Eventually, the pressure in both chambers 2 and 3 will converge to the same value $p_{up} \cdot V_{up}/(V_{up}+V_{down})$.

FIG. 7 illustrates the permeation process of a vapour 54 over a sufficient amount of a liquid phase 55 through a test sample 4. After a sufficient period of time the vapour 54 saturates the upstream chamber 2 and the pressure in both chambers 2 and 3 will converge to the vapour pressure.

The calculations are based on the following assumptions described in the prior arts:

the upstream chamber 2 with volume $V_{up}$ contains $N_{up}$ gas or vapour molecules giving a concentration of $n_{up}=N_{up}/V_{up}$ the downstream chamber 3 with volume $V_{down}$ contains $N_{down}$ molecules giving a concentration of $n_{down}=N_{down}/V_{down}$ the test sample 4 between the upstream chamber 2 and the downstream chamber 3 and the whole gas container 1 are neither sink for nor source of molecules upstream chamber 2, test sample 4 and downstream chamber 3 have the same temperature initially (t=0) the downstream chamber 3 is at a sufficiently low vacuum level $n_{down}=0$ In the case of a gas the upstream chamber 2 is initially filled with gas to $P_{up}$. In the case of vapour over a liquid the upstream chamber 2 is at the constant vapour pressure of the liquid during the measurement.

The driving force for permeation of a gas or vapour through a material such as a film is the concentration difference between the two sides of the test sample 4.

$$\frac{dn_{down}}{dt} = c_1(n_{up} - n_{down}) \quad (1)$$

with $c_1$ a constant. During the permeation process gas molecules permeate from the upstream chamber 2 to the downstream chamber 3.

In the case of gas permeation $n_{up}$ decreases and $n_{down}$ increases during the permeation measurement. As the gas is not replenished in the upstream chamber 2, the total amount of gas molecules $N_0=N_{up}+N_{down}$ is a constant. Equation (1) can be rewritten:

$$\frac{dn_{down}}{dt} = c_1\left(\frac{N_0 - n_{down} \cdot V_{down}}{V_{up}} - n_{down}\right) \quad (2)$$

The solution of the differential equation (2) with the constraint $n_{down}(t=0)=0$ is:

$$n_{down}(t) = \frac{N_0}{V_{up} + V_{down}}\left(1 - e^{-\tau\left(1+\frac{V_{down}}{V_{up}}\right)t}\right) \quad (3)$$

with $\tau$ the exponential parameter. Usually, the rate of gas permeation is desired for the pressure at t=0. Equation (3) is differentiated with respect to t and the value is taken at t=0:

$$\left.\frac{dn_{down}}{dt}\right|_{t=0} = \tau \cdot \frac{N_0}{V_{up}+V_{down}}\left(1+\frac{V_{down}}{V_{up}}\right) \quad (4)$$

With n=N/V equation (4) yields:

$$\left.\frac{dN_{down}}{dt}\right|_{t=0} = \tau \cdot \frac{N_0 \cdot V_{down}}{V_{up} + V_{down}}\left(1 + \frac{V_{down}}{V_{up}}\right) \quad (5)$$

Equation (5) gives the rate of gas permeation. $V_{down}$, $V_{up}$ are known parameters of the experimental set-up; $N_0$ can be calculated from the pressure $V_{up}$ was filled at, the temperature T and $V_{up}$. In a similar way, the decrease of the upstream pressure can be used to determine the same exponential parameter $\tau$. To obtain the rate of permeation the exponential parameter $\tau$ needs to be estimated. An example is given in the next paragraph.

In the case of a vapour over a liquid phase $n_{up}$ is a constant and the solution of the differential equation (1) with $n_{down}$ (t=0)=0 is:

$$n_{down}(t) = n_{up}(1 - e^{-\tau \cdot t}) \quad (6)$$

with $\tau$ the exponential parameter. Equation (6) is differentiated with respect to t at t=0 and using n=N/V yields:

$$\left.\frac{dN_{down}}{dt}\right|_{t=0} = \tau \cdot V_{down} \cdot n_{up} = \tau \cdot N_{up} \cdot \frac{V_{down}}{V_{up}} \quad (7)$$

Equation (7) gives the rate of vapour permeation. $V_{down}$ is a known parameter; $n_{up}$ is the vapour concentration of the saturated vapour pressure, which can be obtained from tables for the prevailing temperature. To obtain the rate of permeation the exponential parameter $\tau$ needs to be estimated. An example is given in the next paragraph.

There may be test samples and permeant gases and vapour, which do not satisfy the assumptions used to develop equations (6) and (7). For example, if the material of the test sample swells or other processes known to those skilled in the art are important, the fit with a single exponential function may not be sufficient. In this case, a more general approach to the problem can be taken by measuring the pressure in the downstream chamber 3 and upstream chamber 2 as function of time and developing an empirical function to fit these experimental data. In subsequent experiments the gas container 1 with the test sample 4 may be detached and pressure measurements taken as described. These experimental data are then used as input to the empirical approximation function to calculate the rate of permeation.

3. Examples

Permeation measurements were carried out on test samples of oriented polypropylene (OPP) and polyethylene terephthalate (PET), which are materials widely used for packaging. The purpose of the measurement was the determination of the rate of permeation of a gas or vapour through the test sample 4. During the measurement the pressure in the downstream chamber 3 was measured. The measured data points are approximated by an exponential function with the exponential parameter $\tau$. This exponential parameter is used as input for equation (5) in the case of a gas and equation (7) in the case of a vapour.

In the first example the permeation of oxygen through a 60 μm thick test sample of OPP with an exposed area of 50 cm² was studied at a temperature of about 81° C. The upstream chamber 2 was initially filled with oxygen 60 from a gas bottle 9 through valve 6 at a pressure of 0.26 bar.

FIG. 8 shows two experimental curves 60, 61 and two curves where the experimental data have been approximated by an exponential function 62, 63. The dotted line 60 is the downstream pressure $p_{down}$ and the continuous line 62 is the upstream pressure $p_{up}$. The circles 61 are the approximations for the downstream pressure and the squares 63 are approximations for the measured upstream pressure 62. The exponential parameters are $\tau_{down}$=0.0014 min$^{-1}$ and $\tau_{up}$=0.0014 min$^{-1}$. The pressure in the downstream chamber 3, the pressure in the upstream chamber 2 or both can be used to estimate the exponential parameter $\tau$.

FIG. 9 shows the data from curves 60, 61, 62 and 63 (FIG. 8) in a logarithmic representation. In logarithmic representation the experimental data can be approximated with a straight line. The slope of the curves in FIG. 9 is the exponential parameter $\tau$ from equation (5) which can be obtained from two points 64 and 65. For the pressure in the upstream chamber 2 one of the points can be the initial (filling) pressure 64 of the upstream chamber 2. For the downstream pressure one of the points can be the equilibrium pressure. For example a data point could be taken at t=1000 min. From FIG. 9 the slope can be determined as (4.6−3.2)/1000 min=0.0014 min$^{-1}$. FIG. 9 shows, that from about 1700 min onwards the signal to noise ratio deteriorates. The data point needed for the determination of the slope $\tau$ should be taken from an area, where the signal to noise ratio is still sufficiently high.

With $p_{up}$ of initially 0.26 bar and $V_{up}$=$V_{down}$=76 cm³ $N_0$ is 4.1·10²⁰ cm$^{-3}$. Equation (5) gives a rate of permeation through the area of the sample of 0.014 min$^{-1}$·4.1·10²⁰ cm$^{-3}$=5.8·10$^{17}$ min$^{-1}$. Normalizing this value to an area of 1 m² and an upstream pressure of 1 bar and expressing the time in days and the amount of oxygen in cm³$_{STP}$ the rate of permeation in this example is 6200 cm³$_{STP}$/m²/d/bar in agreement with known data.

In the second example the permeation of saturated water vapour through a 38 μm thick test sample of PET with an exposed area of 50 cm² was studied at room temperature. The upstream chamber 2 was filled with saturated water vapour 61.

FIG. 10 shows the measured downstream pressure $p_{down}$ as continuous line 70. The dotted line 71 represents a curve fitted according to equation (6) with an exponential parameter $\tau$ of 0.011 min$^{-1}$. The dashed line 72 is the saturated water vapour pressure of 22.8 mbar at 20° C. in the upstream chamber 3.

FIG. 11 shows the difference between the saturated water vapour pressure and the measured data from FIG. 10 in a logarithmic representation. In agreement with the described mathematical algorithm the experimental data 70 are in good approximation on a fitted straight line 71 in logarithmic representation. The slope of this straight line is the exponential parameter $\tau$ from equation (6) which can be obtained from two points. In this case, one of the points can be the saturated water vapour pressure 72, which can be found in standard tables. This means, only one other experimental point is needed to determine the exponential parameter $\tau$. For example, a data point 73 can be taken at t=150 min which gives a slope of (3.2−1.5)/150 min=0.011 min$^{-1}$.

With a downstream volume $V_{down}$=76 cm³ $n_{up}$ is 5.7·10$^{17}$ cm$^{-3}$. Equation (7) gives the rate of permeation through the area of the sample as 76 cm³·0.011 min$^{-1}$·5.7·10$^{17}$ cm$^{-3}$=4.8·10$^{17}$ min$^{-1}$. Normalizing this value to an area of 1 m², expressing the time in days and expressing the amount of water vapour in g the rate of permeation is 4.1 g/m²/d in agreement with known data.

For a relative humidity of less than 100%, which can be created in a conventional way for example by using salt solutions, the experiment and the calculations can be carried out in a similar way.

The two examples given above illustrate, that after filling the upstream chamber 2 the gas container 1 can be detached from the sensor(s) 10 and (14). Later one or more pressure readings are taken after attaching the gas container 1 to the sensor(s) 10 and (14).

In the third example the estimation of the solubility S of a test sample of polyethylene naphthalate (PEN) is illustrated. The test sample 4 was first saturated with water and then the outgassing of the water vapour was measured. FIG. 12 shows the pressure as function of time. The water vapour in the downstream chamber 2 was removed every 10 minutes for 12 seconds by means of a pump 5. The removal of the water vapour caused a pressure drop $\Delta p$ as shown in FIG. 12. Because water vapour is removed, the driving force for outgassing is reduced and hence the amount of water vapour released from the sample per evacuation cycle $\Delta p$ is decreasing. Usually the evacuation proceeds for a preset duration or until a preset pressure is reached.

FIG. 13 shows subsequent pressure drops $\Delta p_i$ as function of evacuation cycle i. The experimental data 80 have been approximated by the sum of two exponential functions. The area under the curves 80 and 81 in FIG. 13 is a measure for the amount of water vapour initially present in the sample. A value of about $S=0.005$ $g_{water\ vapour}/g_{polymer}$ has been estimated for the solubility S from the data shown in FIG. 13.

What is claimed is:

1. A method of measuring the rate of permeation of a gas or a vapour including water vapour through a material comprising:

providing a test sample made of the material in a gas container between the upstream chamber with volume $V_{up}$ and a downstream chamber with volume $V_{down}$ of the gas container;

providing a means to remove gas or vapour from the upstream chamber and the downstream chamber;

providing an amount of gas or vapour in the upstream chamber of the gas container;

providing one or more sensors in communication with the upstream chamber and downstream chamber for pressure measurement as a function of time;

approximating the experimental pressure data with an exponential function with an exponential parameter $\tau$;

wherein if it is a gas calculating the rate of permeation $dN_{down}/dt$ from the exponential parameter and the amount of gas $N_0$ according to $$\left.\frac{dN_{down}}{dt}\right|_{t=0} = \tau \cdot \frac{N_0 \cdot V_{down}}{V_{up} + V_{down}}\left(1 + \frac{V_{down}}{V_{up}}\right).$$

wherein if it is a vapour calculating the rate of permeation $dN_{down}/dt$ from the exponential parameter and the amount of water vapour $N_{up}$ according to $$\left.\frac{dN_{down}}{dt}\right|_{t=0} = \tau \cdot N_{up} \cdot \frac{V_{down}}{V_{up}}.$$

2. The method as claimed in claim 1 wherein the test sample is a film.

3. The method as claimed in claim 1 where the exponential parameter $\tau$ is determined from one measured pressure value and the gas pressure the upstream chamber is initially filled at.

4. The method as claimed in claim 1 where the exponential parameter $\tau$ is determined from one measured pressure value and the vapour pressure of the vapour.

5. The method as claimed in claim 1 wherein, after the step of calculating the rate of permeation the method further comprises:

removing the gas or vapour from the upstream chamber and the downstream chamber;

measuring successive pressure increases in the upstream and downstream chamber over successive increments of time;

adding the incremental pressure increases to obtain a total pressure increase;

calculating a total amount of gas or vapour outgassed from the sample using the total pressure increase and the ideal gas law.

* * * * *